US008512228B2

(12) United States Patent  
Vargas

(10) Patent No.: US 8,512,228 B2
(45) Date of Patent: Aug. 20, 2013

(54) RIGIDIZABLE LINKAGE MECHANISMS AND SYSTEMS FOR MODIFYING AN ARTICULATING FORCE

(75) Inventor: Jaime S. Vargas, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/292,470

(22) Filed: Nov. 9, 2011

(65) Prior Publication Data

US 2012/0123207 A1 May 17, 2012

Related U.S. Application Data

(62) Division of application No. 10/899,561, filed on Jul. 27, 2004, now Pat. No. 8,075,476.

(51) Int. Cl.
*A61B 1/00* (2006.01)
(52) U.S. Cl.
USPC .......................... 600/114; 600/144; 600/146
(58) Field of Classification Search
USPC .................................. 600/139–152
See application file for complete search history.

(56) References Cited

U.S. PATENT DOCUMENTS

| 4,066,071 A * | 1/1978 | Nagel ........................... 600/102 |
| 4,550,715 A | 11/1985 | Santangelo et al. |
| 4,601,283 A | 7/1986 | Chikama |
| 4,610,242 A | 9/1986 | Santangelo et al. |
| 4,655,257 A | 4/1987 | Iwashita |
| 4,683,879 A | 8/1987 | Williams |
| 4,762,119 A | 8/1988 | Allred, III |
| 4,909,787 A | 3/1990 | Danforth |
| 4,946,443 A | 8/1990 | Hauser et al. |
| 5,174,276 A | 12/1992 | Crockard |
| 5,179,935 A * | 1/1993 | Miyagi ........................ 600/142 |
| 5,251,611 A | 10/1993 | Zehel et al. |
| 5,337,733 A | 8/1994 | Bauerfeind et al. |
| 5,372,587 A | 12/1994 | Hammerslag et al. |
| 5,448,989 A | 9/1995 | Heckele |
| 5,482,029 A | 1/1996 | Sekiguchi et al. |
| 5,607,386 A | 3/1997 | Flam |
| 5,713,870 A | 2/1998 | Yoon |
| 5,759,151 A | 6/1998 | Sturges |
| 5,779,624 A | 7/1998 | Chang |
| 5,846,181 A | 12/1998 | Heckele et al. |
| 5,916,146 A | 6/1999 | Allotta et al. |
| 5,916,147 A | 6/1999 | Boury |
| 5,944,690 A | 8/1999 | Falwell et al. |

(Continued)

OTHER PUBLICATIONS

Vertut, Jean and Phillipe Coiffet, *Robot Technology: Teleoperation and Robotics Evolution and Development*, English translation, Pretence-Hall, Inc., Inglewood Cliffs, NJ, USA 1986, vol. 3A, 332 pages.

*Primary Examiner* — Matthew J Kasztejna

(57) ABSTRACT

A rigidizable linkage mechanism comprises a plurality of serially arranged links comprising a distal link and a link proximal to the distal link. The rigidizable linkage mechanism further comprises a cable that extends in a distal direction through the plurality of serially arranged links, extends around the distal link of the plurality of links, and in a proximal direction back through at least a portion of the plurality of links. A distal end of the cable is fixedly coupled to the link proximal to the distal link, and a proximal end of the cable is coupled to a rigidizing actuator.

20 Claims, 18 Drawing Sheets

(56) References Cited

U.S. PATENT DOCUMENTS

| | | | |
|---|---|---|---|
| 6,013,024 A * | 1/2000 | Mitsuda et al. | 600/146 |
| 6,090,121 A | 7/2000 | Weber et al. | |
| 6,146,355 A | 11/2000 | Biggs | |
| 6,344,038 B1 | 2/2002 | Weber | |
| 6,468,203 B2 | 10/2002 | Belson | |
| 6,520,954 B2 | 2/2003 | Ouchi | |
| 6,695,772 B1 | 2/2004 | Bon et al. | |
| 6,790,173 B2 | 9/2004 | Saadat et al. | |
| 6,817,974 B2 * | 11/2004 | Cooper et al. | 600/142 |
| 6,945,956 B2 | 9/2005 | Waldhauser et al. | |
| 6,960,163 B2 | 11/2005 | Ewers et al. | |
| 7,241,263 B2 | 7/2007 | Boulais | |
| 7,320,700 B2 * | 1/2008 | Cooper et al. | 606/205 |
| 2003/0233025 A1 | 12/2003 | Saadat et al. | |
| 2003/0233026 A1 | 12/2003 | Saadat et al. | |
| 2003/0233027 A1 | 12/2003 | Ewers et al. | |
| 2003/0233057 A1 | 12/2003 | Saadat et al. | |
| 2003/0233058 A1 | 12/2003 | Ewers et al. | |
| 2003/0233066 A1 | 12/2003 | Ewers et al. | |
| 2004/0138529 A1 | 7/2004 | Wiltshire et al. | |
| 2006/0199999 A1 | 9/2006 | Ikeda et al. | |

\* cited by examiner

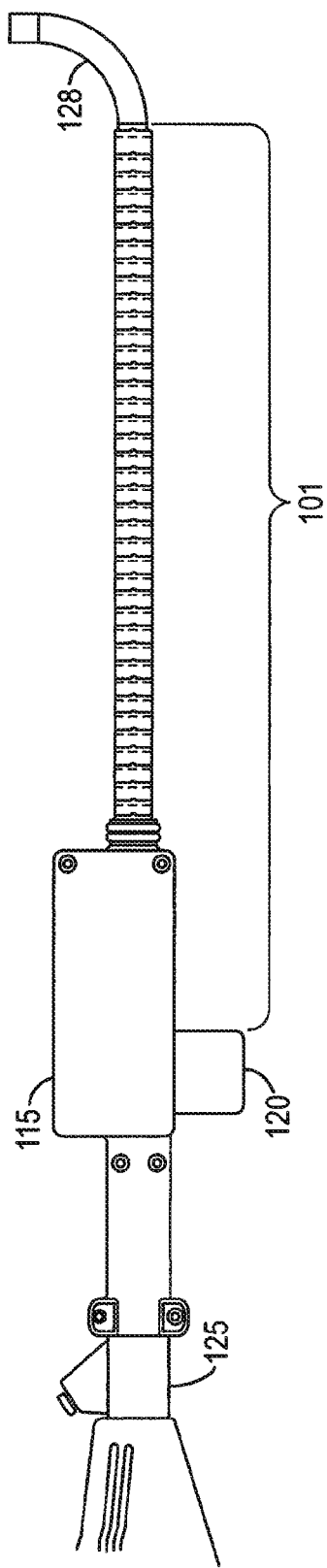
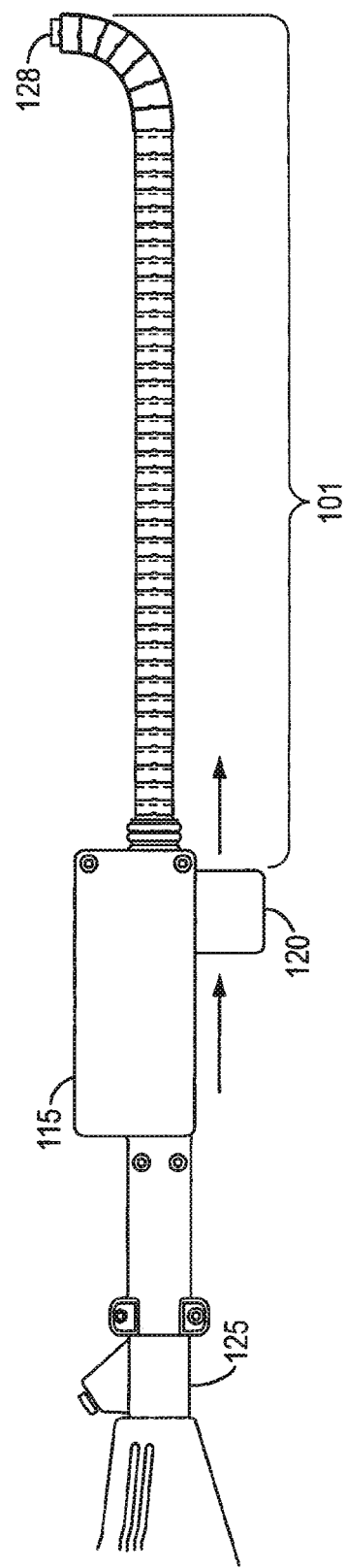
FIG. 12A
FIG. 12B

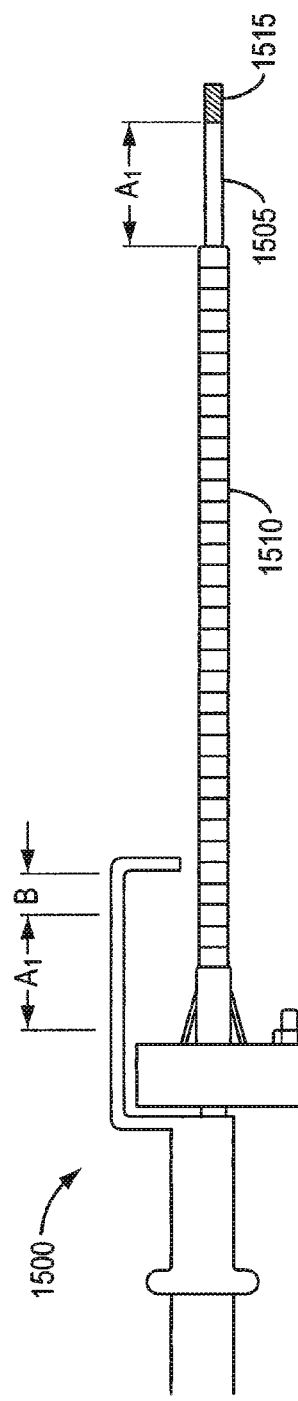
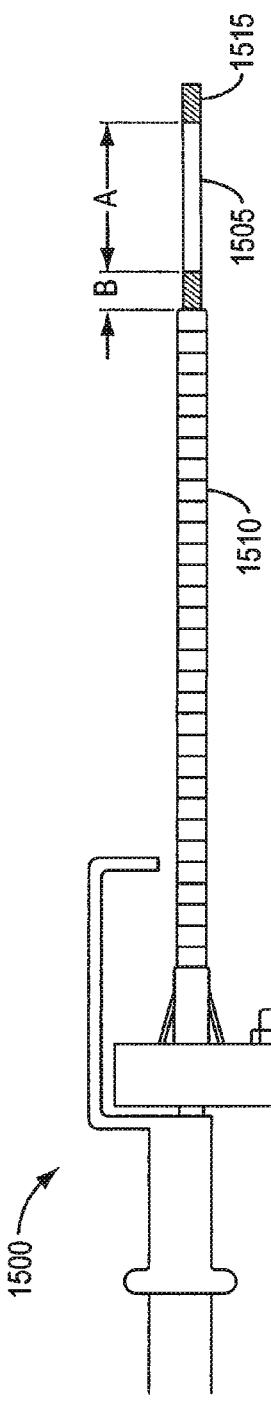
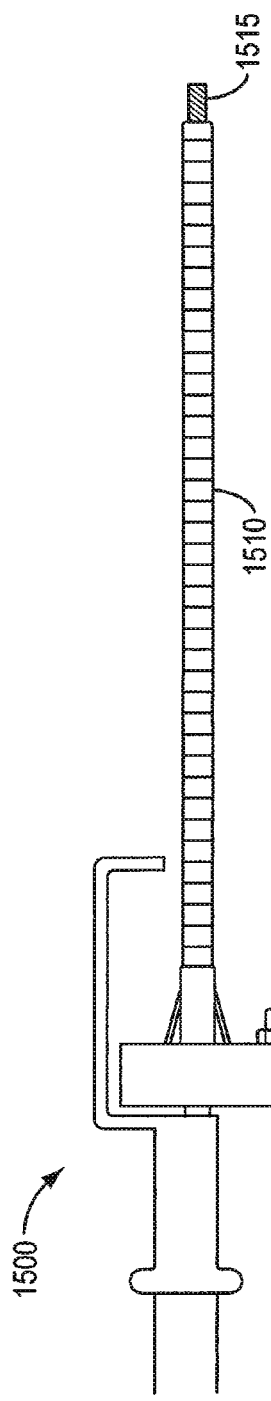
FIG. 15A
FIG. 15B
FIG. 15C

RIGIDIZABLE LINKAGE MECHANISMS AND SYSTEMS FOR MODIFYING AN ARTICULATING FORCE

CROSS-REFERENCE TO RELATED APPLICATIONS

This application is a divisional application and claims the benefit of U.S. patent application Ser. No. 10/899,561 (filed Jul. 27, 2004; now U.S. Pat. No. U.S. Pat. No. 8,075,476 B2), which is incorporated herein by reference in its entirety.

BACKGROUND OF THE INVENTION

1. Field of the Invention

The present invention relates to devices, systems, and processes useful for exploration of hollow body structures, particularly those areas accessed through a tortuous, unsupported path. More particularly, the present invention relates to a system and method for navigation of an endoscope having a steerable tip.

2. Description of Related Art

Endoscopes are frequently used for medical exploratory procedures, either alone or in combination with an overtube for aiding the insertion of the endoscope. When an overtube is used it may be fully inserted in a single step prior to the insertion of the endoscope. The overtube and endoscope may also be incrementally inserted in an alternating fashion.

Overtubes may have a controllable rigidity in order to facilitate their introduction and to provide a firm guide for subsequent insertion of an endoscope. An overtube with controllable rigidity is typically in a relaxed state during its insertion or retraction in order to minimize the force transmitted to the body in which it resides. During the insertion or retraction of an endoscope through the overtube, the overtube is maintained in a rigidized state.

In addition to controllable rigidity, the prior art also teaches the use of a steerable tip for achieving a favorable contact angle between the inserted device and the body in which it is being introduced. Steering may be achieved by the use of control wires or by rotation of the inserted device.

Controllable rigidity and steering in prior art medical exploratory devices are used to minimize the forces applied to the body into which the exploratory device is inserted (e.g., a colon). Steering provides a low contact angle with a body surface and minimized rigidity reduces the force transmitted at sites of contact during movement of the inserted device.

Although the prior art has recognized the desirability of reducing the forces applied to a body being explored, present medical exploratory devices typically depend upon a finite reactive force from the body under investigation during use. Unfortunately, even a reduced contact force has the potential for patient discomfort and tissue trauma.

An example of a potential operator error associated with an incremental advance system is that involving excessive advancement of an endoscope with a steerable tip within a rigidizable overtube. Excessive advancement of the endoscope exposes a section of the endoscope that is not steerable and thus the tip may be inadvertently directed at a large contact angle against the wall of the body being explored. Although the prior art teaches various methods for reducing contact discomfort, a large contact angle resulting from a poorly directed tip may be difficult to overcome. The prior art frequently relies upon excessive advancement in combination with reaction forces from tissue walls to advance an instrument.

An example of a potential operator error associated with an incremental advance system is that involving excessive advancement of an endoscope with a steerable tip within a rigidizable overtube. Excessive advancement of the endoscope exposes a section of the endoscope that is not steerable and thus the tip may be inadvertently directed at a large contact angle against the wall of the body being explored. Although the prior art teaches various methods for reducing contact discomfort, a large contact angle resulting from a poorly directed tip may be difficult to overcome.

Thus, a need exists for system and method for medical exploration that does not depend upon reactive forces from the body being explored. There is also a need for a system prevents operator error through excessive advancement of an insertable device. It is also desirable that such a system be capable of providing free-space navigation interchangeably for endoscopes and other tools.

BRIEF SUMMARY OF THE INVENTION

The present invention combines a cannula with a displacement limiting coupling for attaching to an endoscope or other insertable device. The cannula includes a rigidizable portion and acts as a guide for the inserted device. The displacement limiting coupling establishes functional limits on the relative displacement between the cannula and the insertable device.

In one embodiment of the invention the cannula includes a tubular section coupled to a rigidizable segment. The rigidity of the tubular section is not controlled during operation, whereas the rigidity of the rigidizable segment is controllable.

In a further embodiment the cannula includes a rigidizable segment that is larger in cross-section than the remainder of the cannula. The larger cross-section may be circular or non-circular. The rigidizable segment may be coupled to another rigidizable segment or to a tubular section whose rigidity is not controlled during operation.

In another embodiment the control of the rigidizable segment is provided by a compound cable system that generates a compressive force for rigidization that is greater in magnitude than the tensile force in the cables of the system.

In yet another embodiment the cannula is enclosed by a sheath that is secured at the distal end of the inserted device and at the proximal end of the cannula. The sheath may be secured by an elastic band or by an "o"-ring fitted to a groove.

BRIEF DESCRIPTION OF THE DRAWINGS

FIGS. 12A-12C show the relative positions of the cannula system and an inserted device during an advancement cycle in accordance with an embodiment of the present invention.

FIGS. 15A-15C show a displacement limited coupling with accommodation for cannula compression in accordance with an embodiment of the present invention.

DETAILED DESCRIPTION OF THE INVENTION

Figure 1:
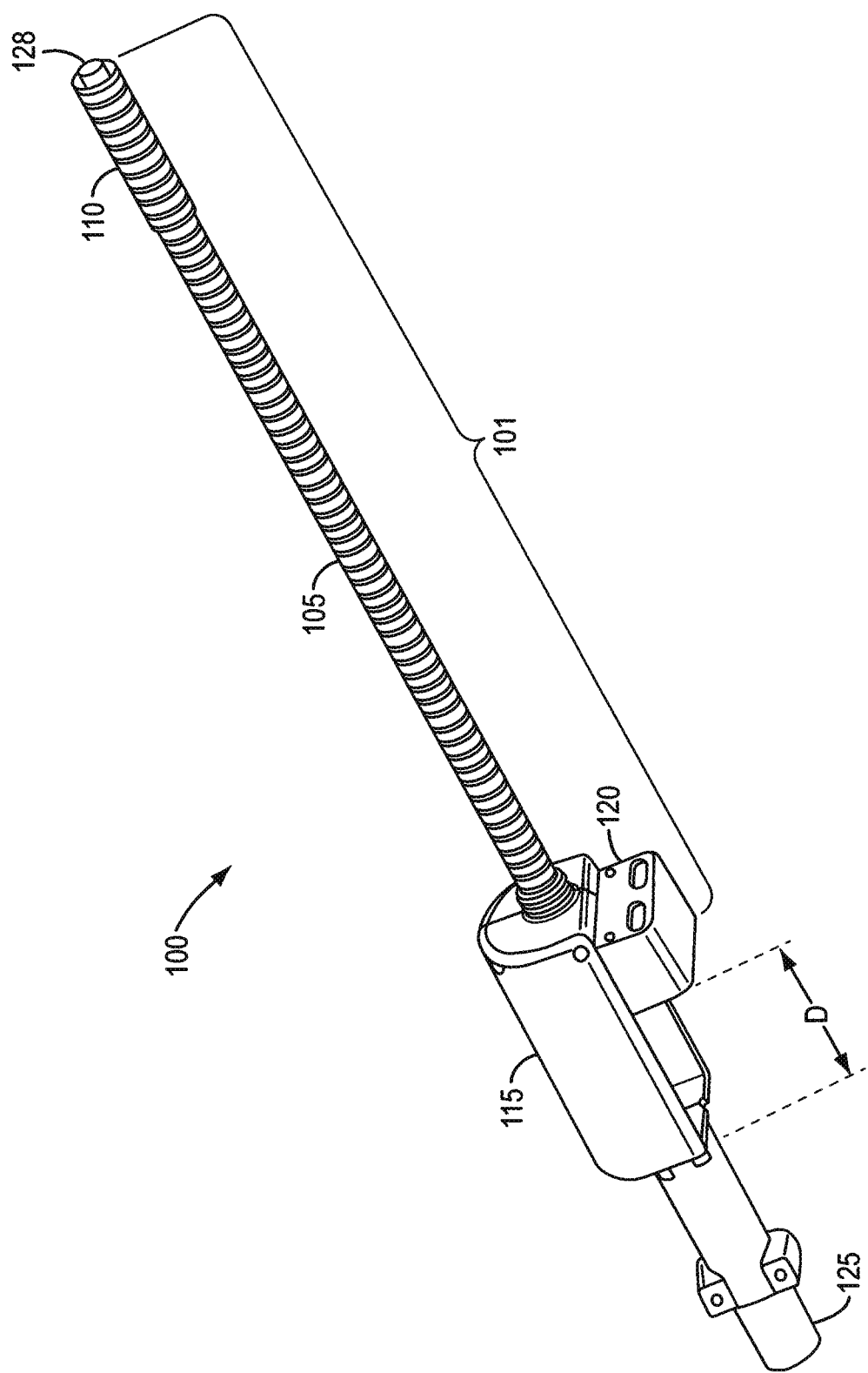
FIG. 1 shows an assembled cannula system in accordance with an embodiment of the present invention.

FIG. 1 shows an embodiment of a cannula system 100. A cannula 101 includes a rigidizing actuator 120. The actuator 120 is used to control the rigidity of the cannula 101. A displacement limiting coupling 115 couples the cannula 101 to an insertable device (e.g., an endoscope) 125. The displacement limiting coupling 115 aligns the axes of the endoscope 125 and the cannula 101, and allows a limited relative axial displacement "D" between the endoscope 125 and the cannula 101. The displacement limiting coupling slidably couples the cannula 101 to the insertable device 125. The insertable device may include a steerable tip 128.

A discussion of rigidizable structures for use in a cannula system may be found in the copending U.S. patent application Ser. No. 10/661,159, "Shape Transferring Cannula System and Method of Use", by the inventor of the present invention, filed Sep. 12, 2003, and is incorporated herein by reference. The cannula 101 may include segments with independently controllable rigidity, or may include a first segment 105 with a cross-section that is different from a second segment 110. In particular embodiments the second segment 110 is adapted to accommodate a steerable tip 128 of the insertable device 125, wherein the displacement limited coupling maintains an overlap between the steerable tip 128 and the second segment 110. The displacement limited coupling may also act to prevent overlap between steerable tip 128 and the first segment 105.

Figure 2:
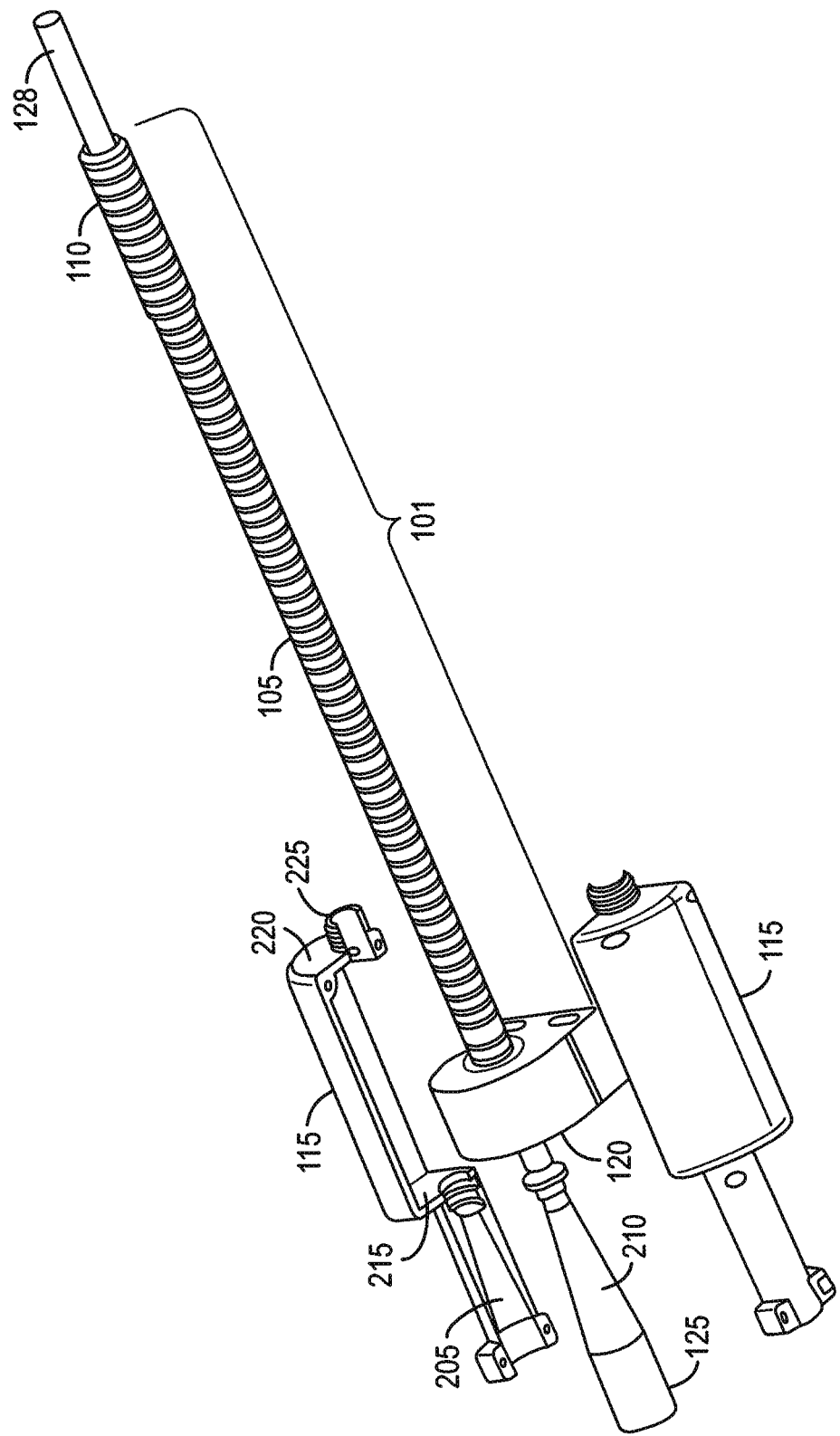
FIG. 2 shows an exploded view of the cannula system shown in FIG. 1.

FIG. 2 shows an exploded view of the cannula system shown in FIG. 1. The displacement limiting coupling 115 has a portion 205 that mates to a surface 210 of the endoscope 125, thus capturing the endoscope 125 and maintaining it in a fixed position with respect to the displacement limiting coupling 115. The displacement limiting coupling 115 also captures the cannula 101. A first wall 215 and a second wall 220 define the limits for the axial travel of the cannula 101. A guide 225 extending from the second wall 220 may be used to support the cannula 101. The difference between the width of the actuator 120 and the distance between the first wall 215 and second wall 220 establishes the maximum allowable axial displacement between the cannula 101 and the endoscope 125. In one embodiment, the range of allowable positions of the endoscope within the cannula 101 is preferably limited to those positions in which the steerable tip 128 is overlapped by the cannula 101.

In one embodiment, the cannula 101 and displacement limiting coupling 115 may be separated from the insertable device 125 without disturbing the coupling between the cannula 101 and the displacement limiting coupling 115. This arrangement facilitates the use of interchangeable or disposable insertable devices, or reusable insertable devices with a disposable cannula system.

Figure 3:
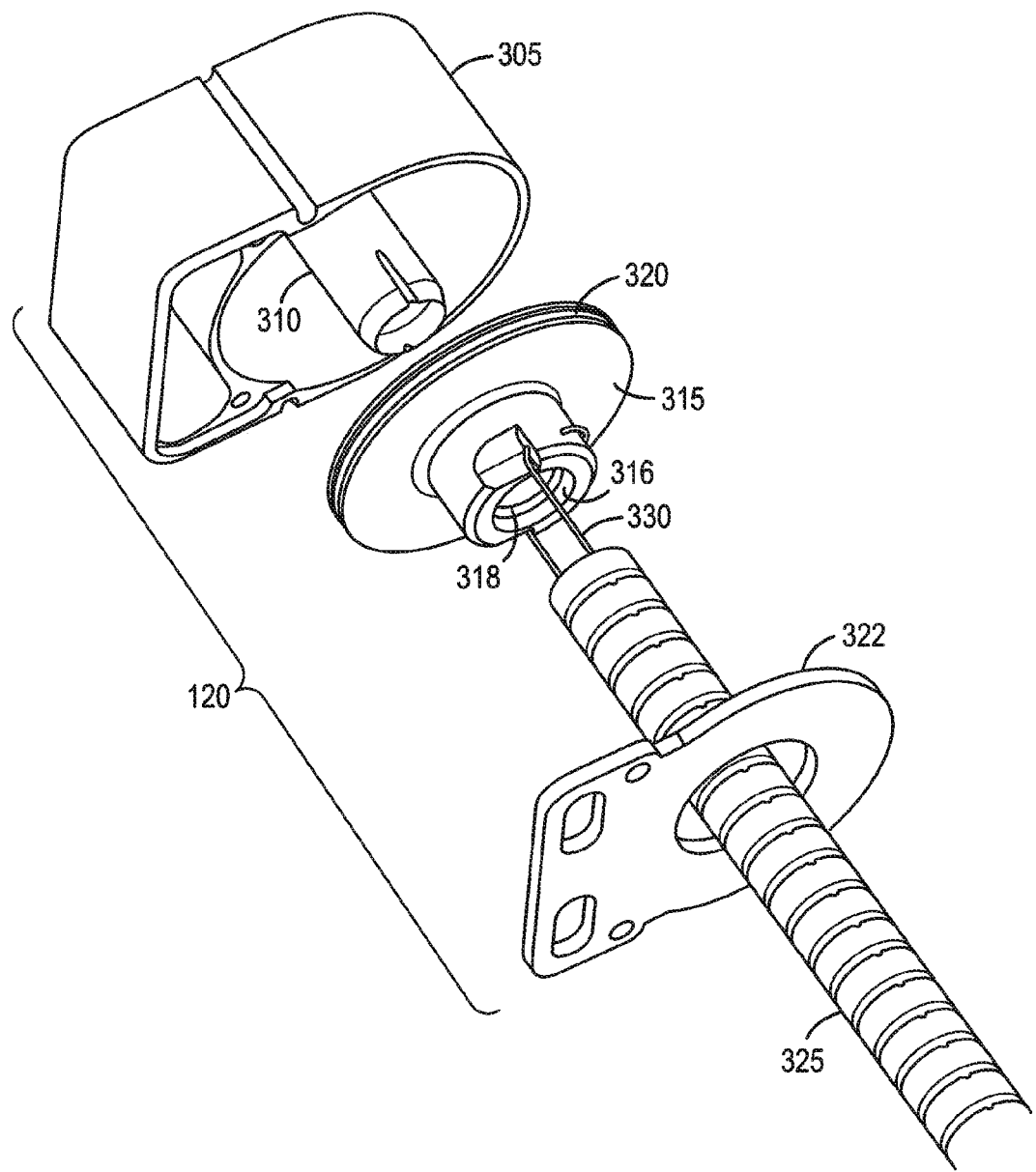
FIG. 3 shows an exploded view of a rigidizing actuator in accordance with an embodiment of the present invention.

FIG. 3 shows an exploded view of the rigidizing actuator 120 of FIG. 2 in accordance with an embodiment of the present invention. A chamber 305 includes a hollow shaft 310. A piston disk 315 having a bore 316 fits over the shaft 310. The piston disk 315 has bore groove 318 and a perimeter groove 320 for accepting "o"-ring seals. In operation, the piston disk 315 is advanced and retracted along the shaft 310 by the application of pressure or vacuum to the chamber 305. The cable 330 may extend from the rigidizing structure 325, loop through the piston 315, and be re-routed back to the rigidizing structure such that the assembly requires only two cable terminations and is self-adjusting with regard to the lengths of cable running through the two cable channels. Cable 330 may be multi-strand cable or a single wire, fiber, or equivalent tension-transmission medium.

The piston disk 316 is coupled to a rigidizing cable 330. Retraction of the piston disk through the application of vacuum produces tension in the cable 330, thus placing the rigidizable section 325 in compression and placing it in a rigidized state. An end plate 322 retains the piston disk 315. The sliding piston disk 316 may be replaced with a flexible bellows to avoid the sliding seals required of piston designs.

Figure 4:
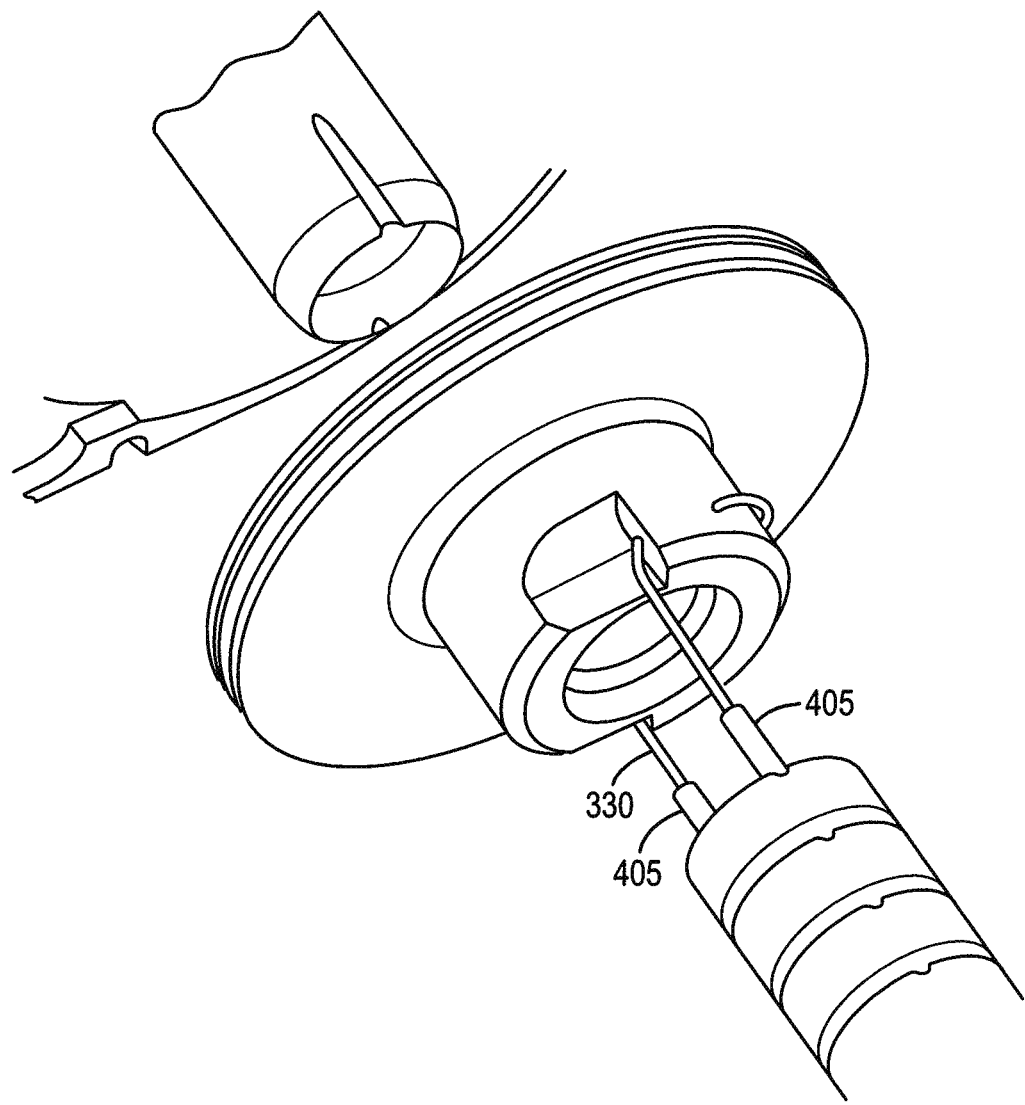
FIG. 4 shows a cannula system with low-friction rigidizing cable sleeves in accordance with an embodiment of the present invention.

FIG. 4 shows an alternative embodiment in which the cable 330 is sheathed in flexible sleeves 405 having a low coefficient of friction. The sleeves improve the rigidizing behavior of the cannula system by minimizing cable drag that can reduce the compressive force produced at the distal end of the cannula 101. In a preferred embodiment the sleeves are fabricated from polytetrafluoroethylene (PTFE). The sleeves 405 may be continuous tubes and run the length of the sheath or may consist of individual PTFE liners for each link.

Figure 5:
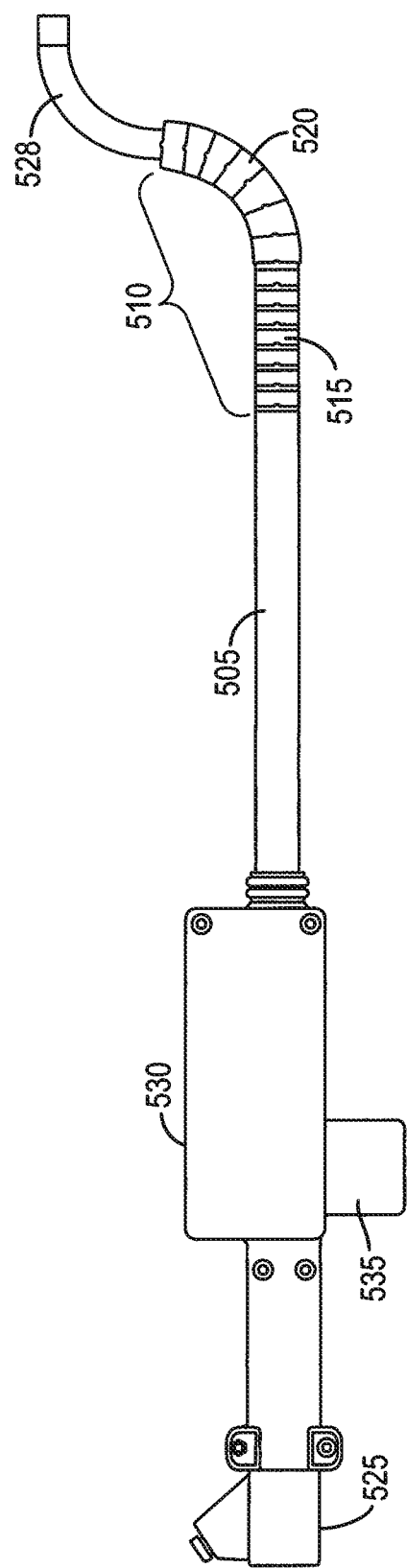
FIG. 5 shows a cannula system having a non-rigidizable-segment in accordance with an embodiment of the present invention.

FIG. 5 shows an embodiment of a cannula system having a flexible non-rigidizable segment 505. In this embodiment the displacement limiting coupling 530, actuator 535 and endoscope 525 are similar to the displacement limiting coupling 115, actuator 120 and endoscope 125 of FIG. 1. The use of the non-rigidizable segment 505 simplifies the cannula system and improves the control over the rigidity of the rigidizable segment 510 of the cannula. In this example the rigidizable segment 510 includes a rigidizable segment 515 with a first cross-section and a rigidizable segment 520 with a second cross-section.

Figure 6:
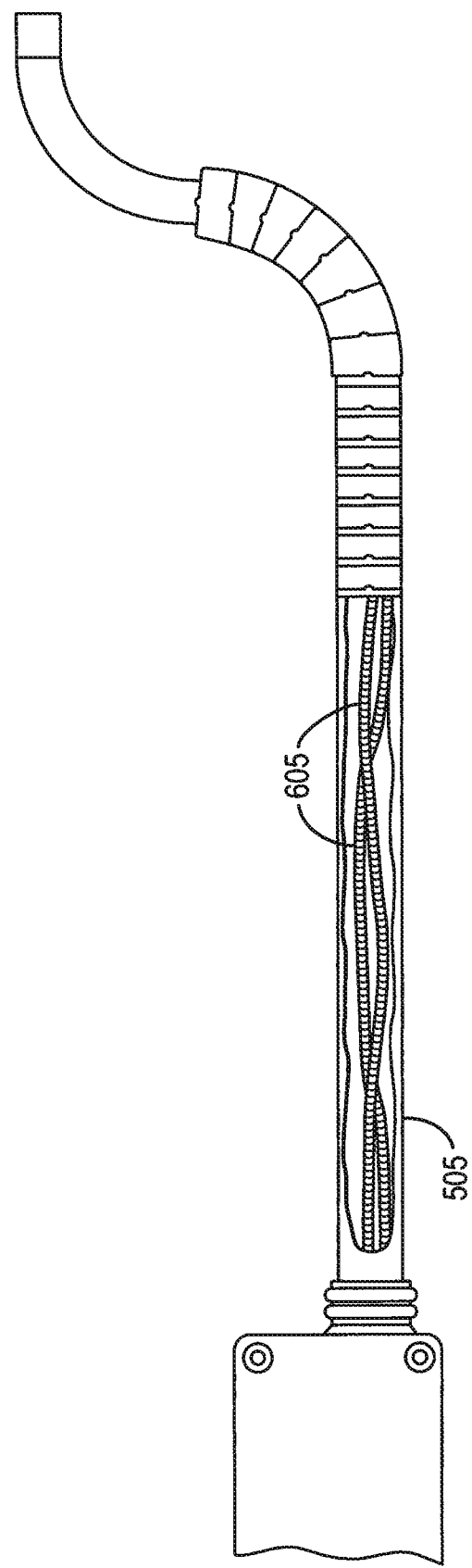
FIG. 6 shows a cutaway view of a portion of the cannula system of FIG. 5 in accordance with an embodiment of the present invention.

FIG. 6 shows a cutaway view of a portion of the cannula system of FIG. 5. Cable guides 605 are used to sheath the rigidizing cable within the non-rigidizable segment 505. In this embodiment the cable guides 605 are fabricated from spiral-wound wire and may have inner and outer liners to reduce friction.

Figure 7:
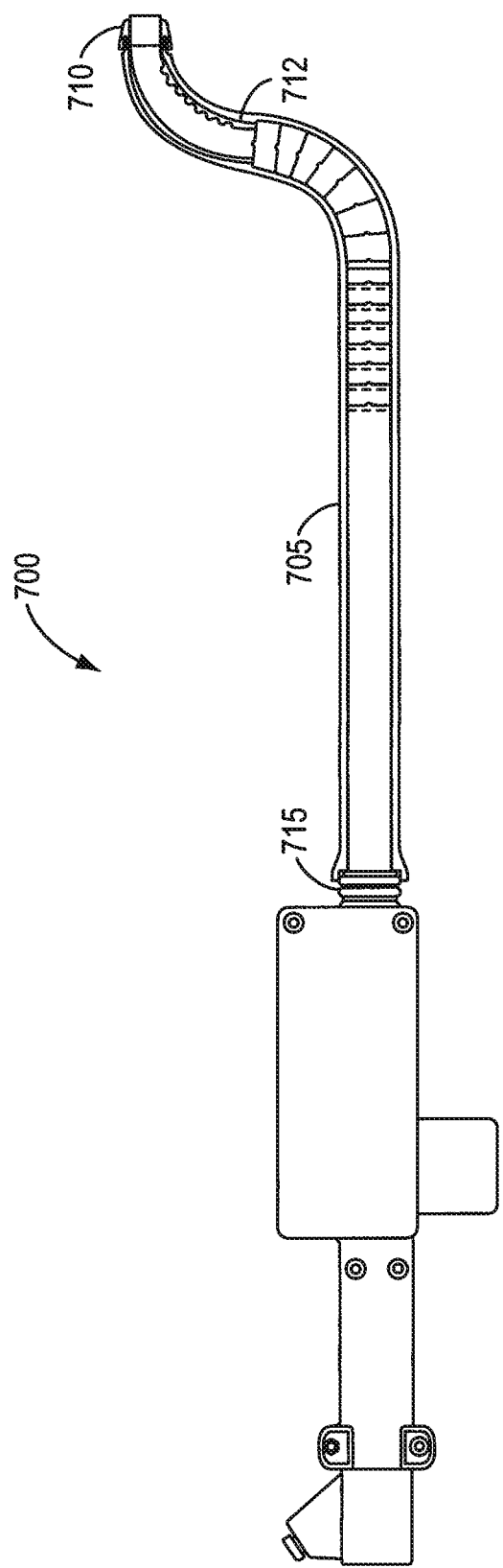
FIG. 7 shows a cannula system with a sheath in accordance with an embodiment of the present invention.

FIG. 7 shows a cannula system 700 with an outer sheath 705 and an inner sheath 712 in accordance with an embodiment of the present invention. The cannula system 700 is similar to that shown in FIG. 5. The addition of the sheath 705 provides a smooth continuous surface that may be used to cover discontinuities. The sheath may also be used to prevent undesired lubrication of rigidizable structures. A flat elastic band is used to provide a seal at the distal end 710 and an "o"-ring is used to provide a seal at the proximal end 715.

Adhesives or heat-shrink materials may also be used to provide sealing at the proximal or distal ends.

Figure 8:
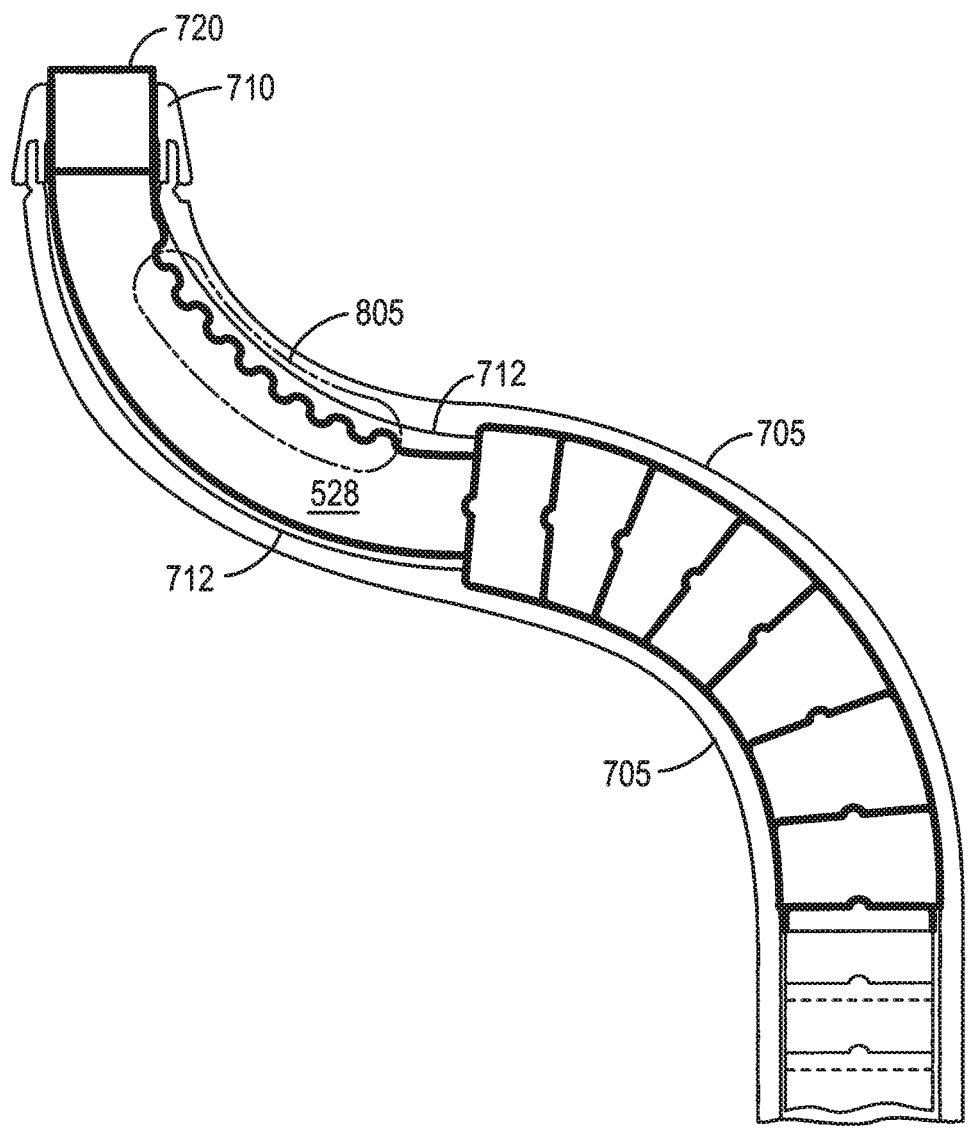
FIG. 8 shows a detailed view of the distal end of the cannula system shown in FIG. 7.

FIG. 8 shows a detailed view of the distal end of the cannula system shown in FIG. 7. Wrinkles 805 may form in the surface of the steerable tip 528 in areas with a negative radius of curvature. The wrinkles 805 may interfere with the smooth advancement and retraction of the tip 720. The inner sheath 712 masks the wrinkles 805 and may be a continuous material or a woven mesh.

Figure 9A:
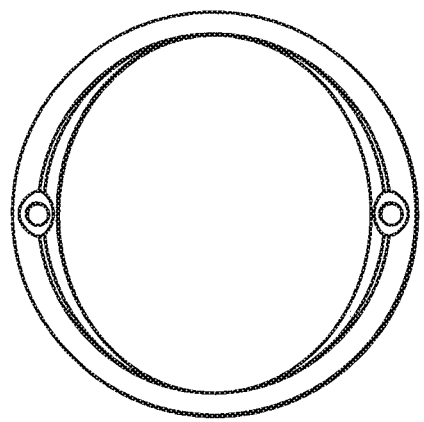
FIGS. 9A and 9B show two views of a non-circular link component of a rigidizable segment in accordance with an embodiment of the present invention.
Figure 9B:
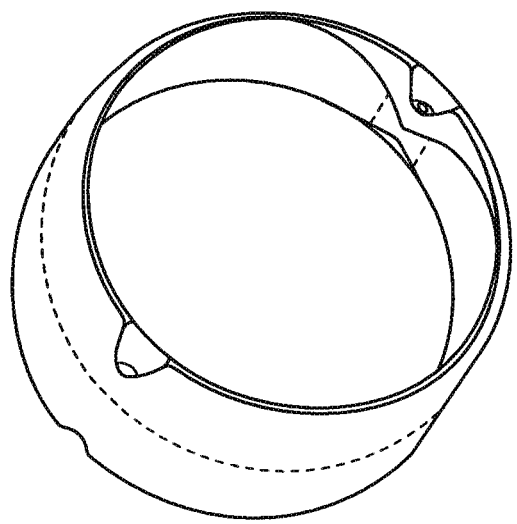

FIGS. 9A and 9B show two views of a non-circular link component for a rigidizable segment such as segment 520 of FIG. 5. An endoscope may have a section with low flexibility adjacent to the steerable tip. The use of a non-circular cross-section link may be used to facilitate the passage of a low-flexibility section while providing a smaller increase in the cross-section than would result from simply increasing the radius of a circular link. A rigidizing segment having non-circular cross-section links may include a terminal distal link with a circular cross-section in order provide more precise direction for an advancing insertable device. The circular cross-section of the terminal distal link may be smaller than that of segment 515 of FIG. 5 in order to maximize the locational accuracy of steering tip 528.

Figure 10A:
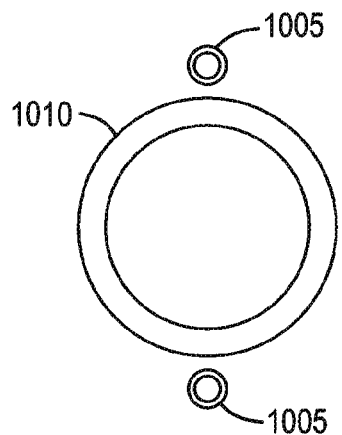
FIGS. 10A-10D show cross-section views of cable sheaths in combination with a non-rigidizable segment in accordance with embodiments of the present invention.
Figure 10B:
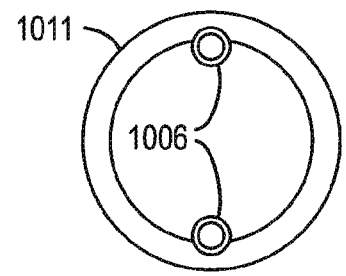
Figure 10C:
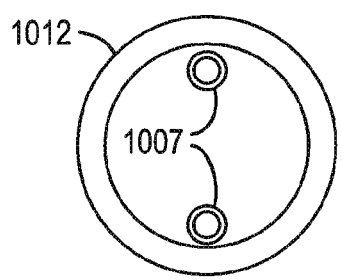
Figure 10D:
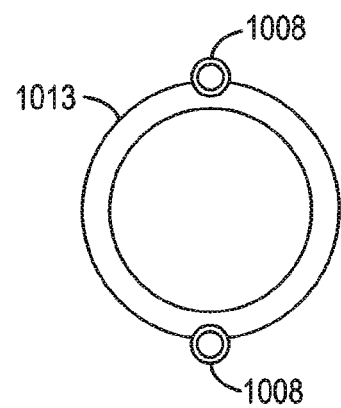

FIGS. 10A-10D show embodiments of a non-rigidizable segment in combination with cable sheaths. FIG. 10A shows unattached cable sheaths 1005 disposed outside of a non-rigidizable segment 1010. FIG. 10B shows attached cable sheaths 1006 disposed inside of a non-rigidizable segment 1011. FIG. 10C shows unattached cable sheaths 1007 disposed inside of a non-rigidizable segment 1012. FIG. 10D shows attached cable sheaths 1006 disposed outside of a non-rigidizable segment 1013. Attached cable sheaths 1006 or 1008 may be formed as a channel within non-rigidizable segments 1011 or 1013.

Figure 11:
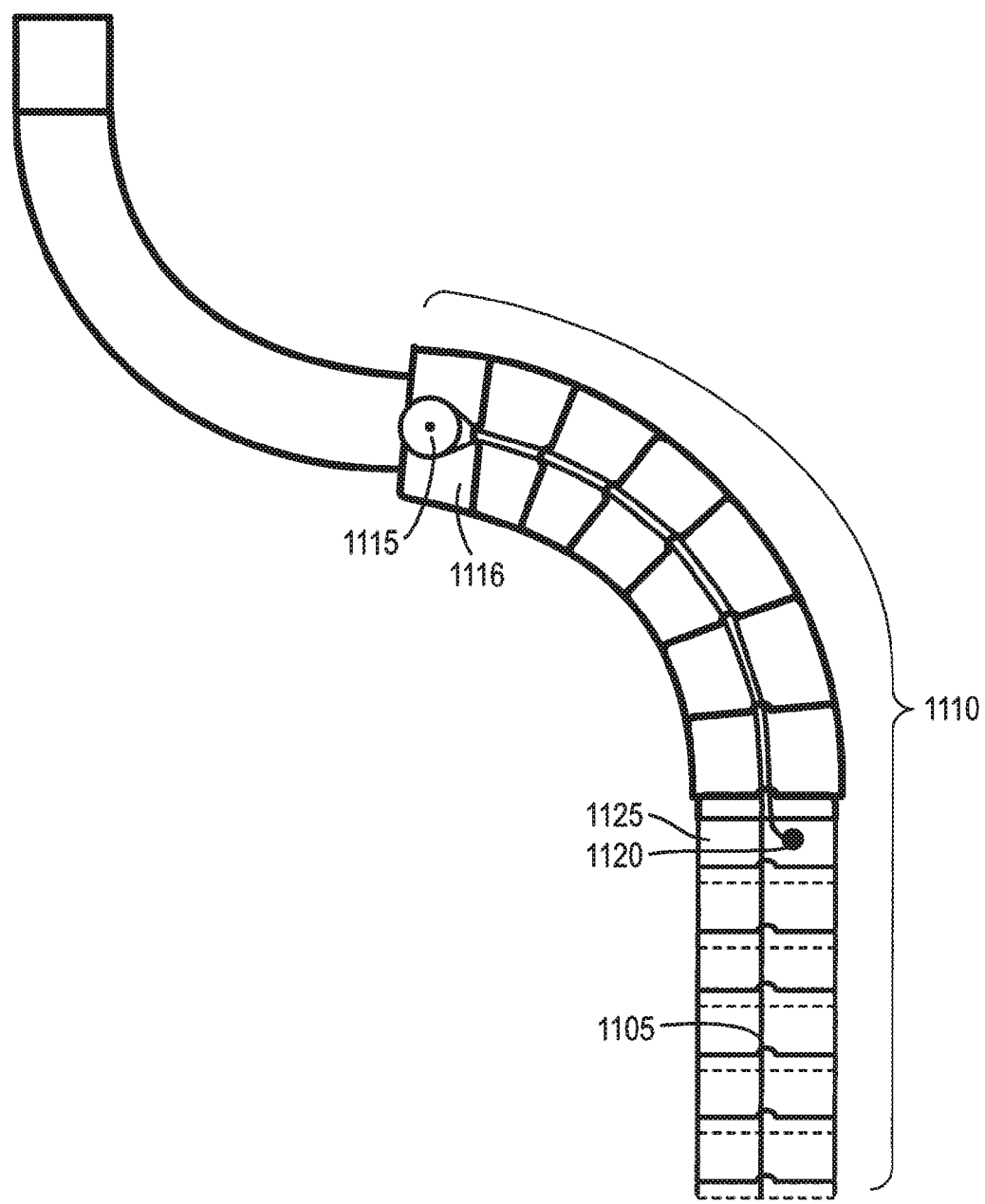
FIG. 11 shows a portion of a cannula system with a compound rigidizing cable linkage in accordance with an embodiment of the present invention.
Figure 17:
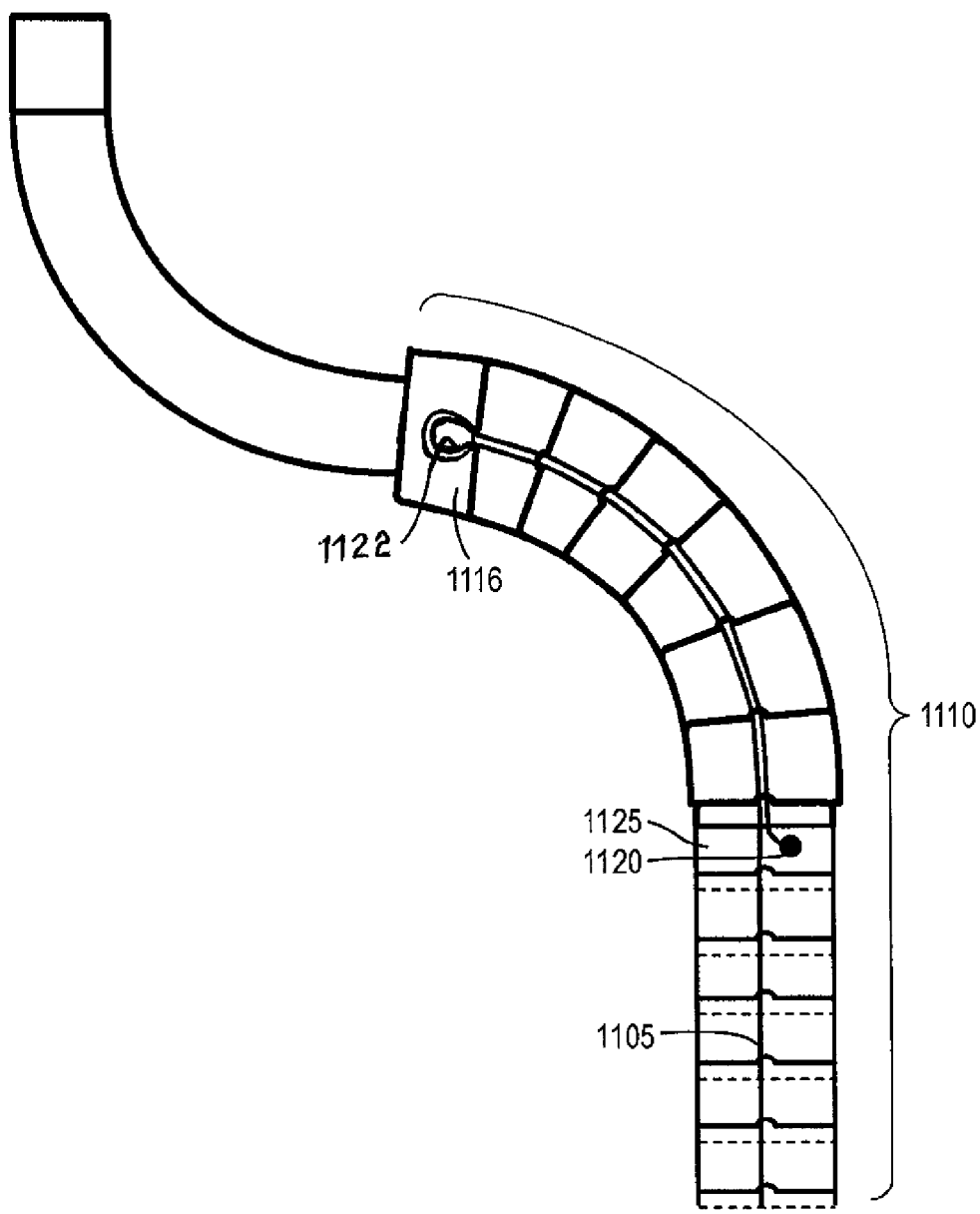
FIG. 17 shows a portion of a cannula system with a compound rigidizing cable linkage having a ferrule or loop back in accordance with an embodiment of the present invention.

FIG. 11 shows a portion of a cannula system with a compound rigidizing cable linkage in accordance with an embodiment of the present invention. A cable section 1105 is shown disposed in a rigidizable segment 1110. The cable section is wrapped around a pulley 1115 associated with a distal link 1116 and routed to an anchor point 1120 associated with an interior link 1125 of the rigidizable segment 1110. The effect of the anchor point 1120 and pulley 1115 is similar to that of a block-and-tackle and results in an increased compressive force on the links between the distal link 1116 and the intermediate link 1125. The compound linkage is thus able to provide a compressive force that is greater in magnitude than the tensile force in the cable. As shown in the exemplary embodiment of FIG. 17, a fixed ferrule or loop back 1122 may be used in place of a pulley at the expense of an increase in friction relative to the pulley. The compound rigidizing cable linkage may be used to compensate for frictional losses and may also be used to reduce the size of the cable used to rigidize the cannula.

Figure 12C:
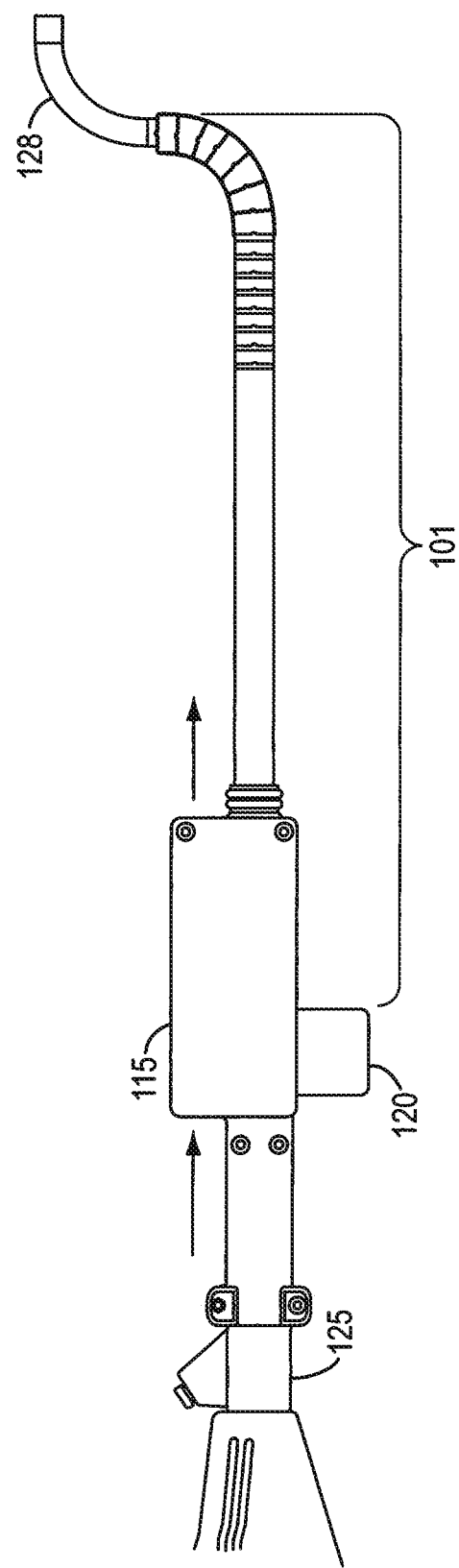

FIGS. 12A-12C show the relative positions of the cannula system and an inserted device during an advancement cycle in accordance with a method embodiment of the present invention. FIGS. 12A-12C are intended to show a cycle of steps that may be repeated as part of a medical exploratory process using a cannula system such as that shown in FIG. 1.

FIG. 12A shows the cannula 101 in a retracted position relative to the steerable tip 128. The actuator 120 is at the left hand limit of the displacement limiting coupler 115 and the cannula 101 maintains a degree of overlap with the steerable tip 128. The cannula is placed in a relaxed state prior to the advancement shown in FIG. 12B, and the steerable tip provides the reactive force that guides the advancing cannula and determines its shape at its distal end.

FIG. 12B shows the cannula 101 advanced over the steerable tip. In this position, the actuator 120 is at the right hand limit of the displacement limiting coupler 115 and steerable tip is largely covered by the cannula 101. The cannula 101 may then be placed into a rigid state prior to the advancement of the endoscope shown in FIG. 12C.

FIG. 12C shows the steerable tip advanced and steered in a new direction. In this position, the actuator 120 is at the left hand limit of the displacement limiting coupler 115 and overlap is maintained between the cannula 101 and steerable tip 128. In advancing the steerable tip, the rigid cannula 101 provides the reactive force that guides the endoscope except for the exposed portion of the steerable tip 128.

A steerable tip may be a specific structure connected to the distal end of an insertable device, or it may be a distal portion of an insertable device having a homogeneous structure. A steerable tip may also be considered to include a coupling that is used to connect it to the remainder of the insertable device. An example of a specific structure is a segment whose bend radius is remotely controllable, or a guidewire having a straight section and a curved section. Alternatively, a guidewire may lack a straight section and have a continuous curve with a variable radius of curvature. For such a guidewire or other insertable device having a homogeneous structure, the preferred length of the steerable tip (section to be overlapped) may defined in relation to the body that is being explored.

For maximum inspection coverage it may be desirable that an endoscope be capable of being retroflexed, that is, being formed into an arc of 180 degrees within the body being inspected. Thus, a steerable tip may be defined as the portion of a homogeneous insertable device that has a bend radius that is less than or equal to one half of the width of the body being explored.

Whether an insertable device employs a distinct structure as a steerable tip, or a section with a bend radius having a particular characteristic, the displacement limiting coupling of the present invention may be used to maintain an overlap between a distal rigidizable segment of a cannula and the steerable tip.

In addition to endoscopic procedures, the cannula system of the present invention may also be used for surgical procedures. Examples of per-oral transgastric peritoneal surgery to which the invention may be applied are organ removal and repair (e.g., transgastric cholycistectomy), gastro-jejunostomy (e.g., jejunum anastomosis to the stomach), and gynecological procedures such as transgastric fallopian tube ligation.

Per-oral transgastric surgery combines flexible endoscopic and surgical skills to do abdominal (peritoneal) surgery through a small stomach incision with per-oral access, and can reduce infection, peritonitis, and surgical adhesions. In contrast, conventional surgery performed through trans-abdominal ports or open incisions can result in significant morbidity and abdominal surgical adhesions. The lack of an external incision can reduce pain and the likelihood of infection, and outpatient abdominal surgeries under only moderate sedation become possible.

The cannula system of the present invention allows navigation in arbitrary directions in and around organs, and with sufficient mechanical support to apply force from the tip of an insertable device when necessary.

In cardiology, transseptal approaches such as percutaneous mitral valve repair and other therapies are currently limited by the positioning and angle-of-attack limitations of current catheter technology. The cannula system of the present invention may be used to provide control over position and angle of attack as well as a stiffer, more stable platform from which to apply force. Navigation to the coronary sinus and atrial fibrillation sites may be performed, as well as unsupported navigation in the atria and ventricles.

Figure 13:
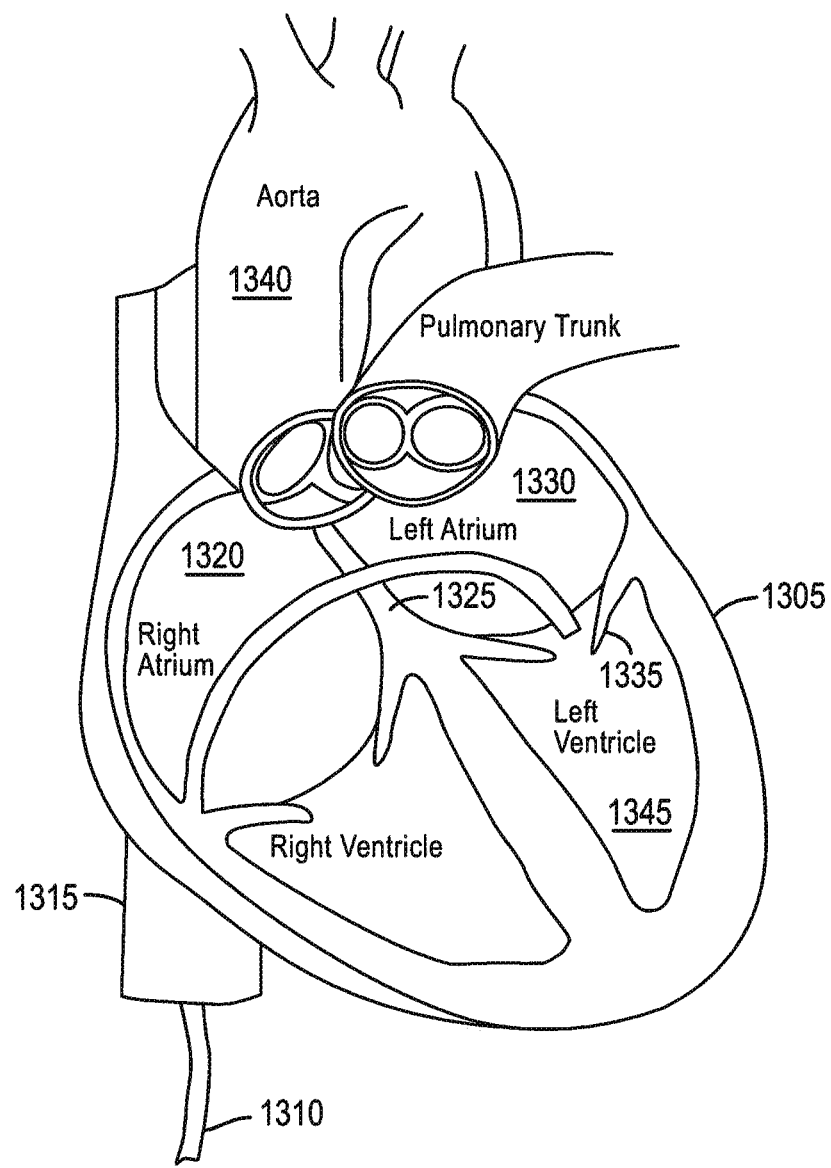
FIG. 13 shows a cutaway view of the heart and a transseptal path for a valvuloplasty.

FIG. 13 shows a cutaway view of a heart 1305 and a transseptal path for a valvuloplasty. The path 1310 passes through the vena cava 1315 and into the right atrium 1320. An insertable device and cannula system may thus be introduced into the right atrium. The cannula system may then be used to control the angle of approach to the septum 1325 and provide support for an insertable device that is used to penetrate the septum 1325 and enter the left atrium 1330. The mitral valve 1335 may then be accessed from within the left atrium. Alternatively, perforation of the septum 1325 may be avoided by unsupported navigation through the aorta 1340 into the left ventricle 1345, and through the mitral valve 1335.

Figure 14:
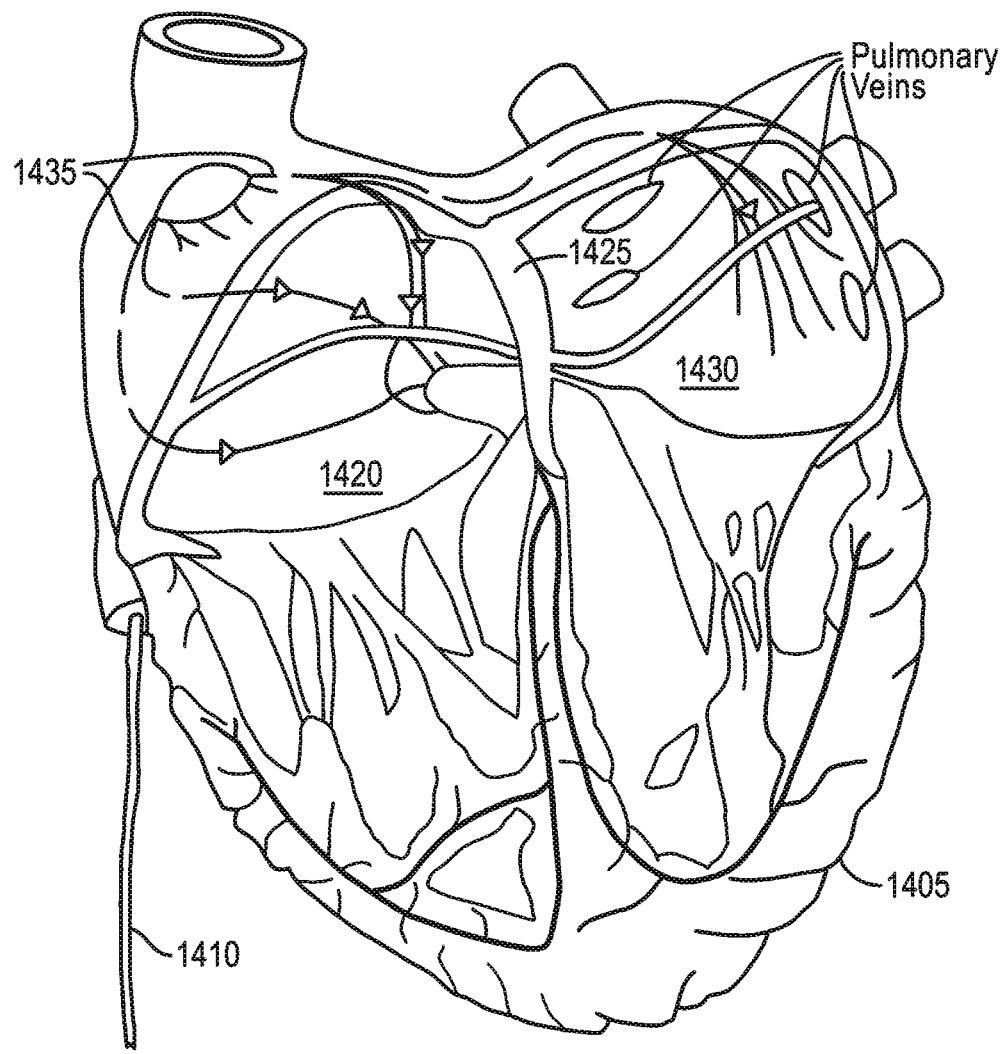
FIG. 14 shows a cutaway view of the heart and a transseptal path for an ablation procedure.

FIG. 14 shows a cutaway view of the heart and a transseptal path for an ablation procedure. The path 1410 passes through the vena cava 1415 and into the right atrium 1420. An insertable device and cannula system may thus be introduced into the right atrium. The cannula system may then be used to control the angle of approach to the septum 1425 and provide support for an insertable device that is used to penetrate the septum 1425 and enter the left atrium 1430. Ablation may then be performed at sites (e.g., pulmonary vein ostia) associated with cardiac electrical pathways 1435.

FIG. 15A shows a cannula system 1500 with a displacement limited coupling with an allowable displacement that is the sum of length $A_1$ and B. Length $A_1$ corresponds to an overlapped active length of a steerable tip 1505. Length B is a length associated with a change in the length of cannula 1510 that may occur during rigidizing of the cannula through axial compression. The cannula 1510 is shown in a relaxed state.

FIG. 15B shows the cannula system 1500 of FIG. 15A with the cannula 1510 in a rigidized state. In the rigidized state, an additional length B of the steerable tip 1505 is exposed.

FIG. 15C shows the rigidized cannula 1510 of FIG. 15B in an advanced position, overlapping length $A_1$ and length B. A non-steerable portion 1515 of the steerable tip 1505 is exposed. Tip portion 1515 may be an optical assembly of an endoscope.

Figure 16:
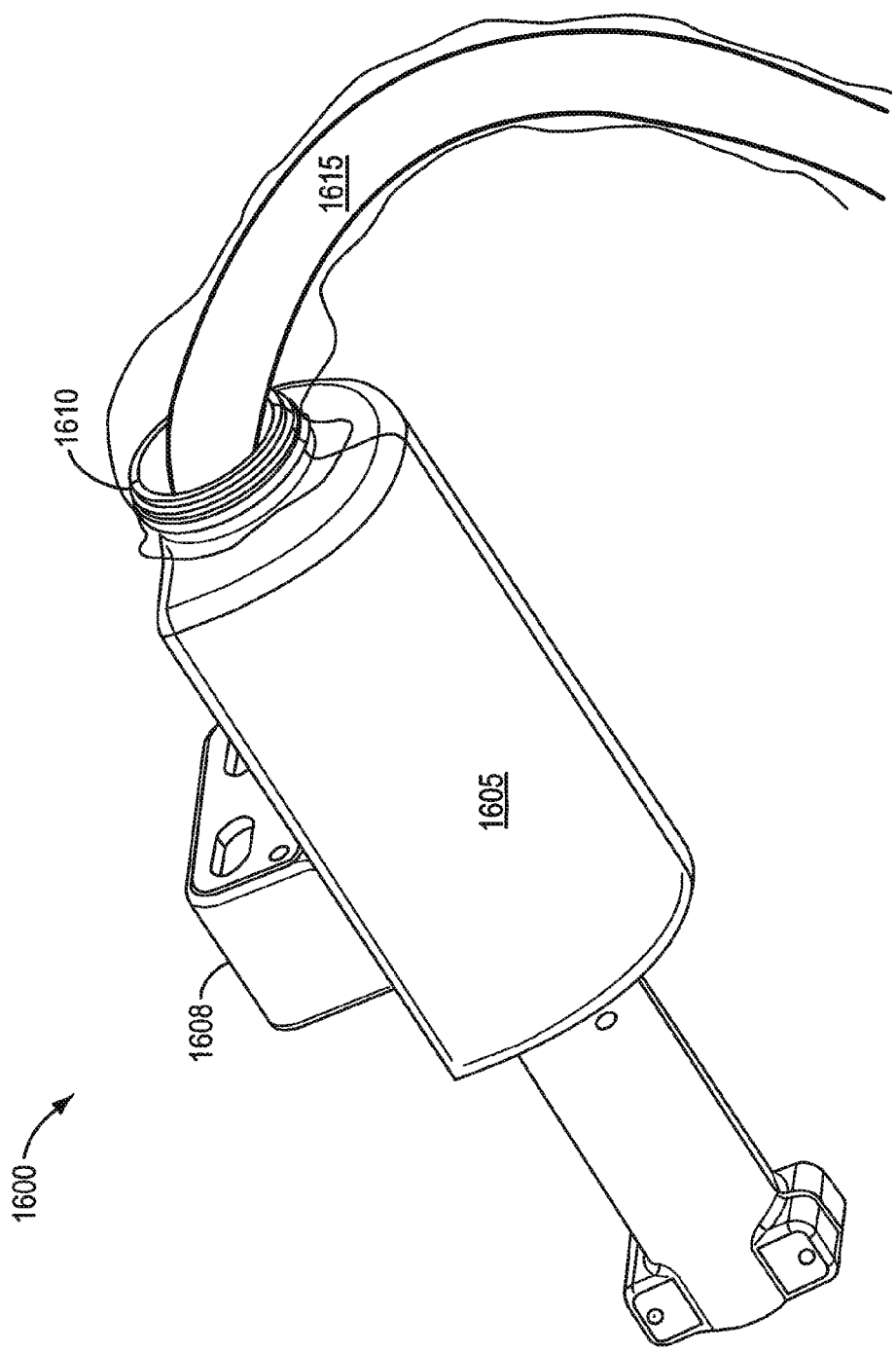
FIG. 16 shows a displacement limited coupling with enhanced clearance for a cannula in accordance with an embodiment of the present invention.

FIG. 16 shows a cannula system 1600 with a displacement limited coupling 1605 having enhanced clearance port 1610 for a cannula 1615. In this embodiment, support for actuator 1608 and cannula 1615 are provided by the body of the displacement limited coupling 1605. The enhanced clearance port 1610 may be used to allow the cannula 1615 to be advanced and retracted when it is in a curved state.

While the invention has been described in detail with reference to preferred embodiments thereof, it will be apparent to one skilled in the art that various changes can be made, and equivalents employed, without departing from the scope of the invention. Specific examples of an actuator for rigidizing a cannula segment and housing walls have been described for limiting relative axial displacement. These specific examples are not exclusive of other applicable structures and methods.

What is claimed is:

1. A rigidizable linkage mechanism comprising:
a plurality of serially arranged links comprising a distal link and a link proximal to the distal link, wherein the plurality of serially arranged links are coupled to move relative to one another to selectively position the plurality of serially arranged links into a curved shape; and
a cable that extends in a distal direction through the plurality of serially arranged links, extends around the distal link of the plurality of serially arranged links, and in a proximal direction back through at least a portion of the plurality of serially arranged links;
wherein a distal end of the cable is fixedly coupled to the link proximal to the distal link and a proximal end of the cable is coupled to a rigidizing actuator.

2. The mechanism of claim 1, wherein the distal end of the cable is fixedly coupled to an intermediate link of the plurality of serially arranged links.

3. The mechanism of claim 1, wherein the distal link comprises a pulley, and wherein the cable extends around the pulley.

4. The mechanism of claim 1, wherein the distal link comprises a fixed ferrule or loop back, and wherein the cable extends around the fixed ferrule or loop back.

5. The mechanism of claim 1, wherein the plurality of serially arranged links are at least part of a cannula.

6. The mechanism of claim 5, wherein the cannula is configured to receive a device and to interact with a limiting coupling affixed to the device to prevent the cannula from sliding over the device beyond a preestablished proximal limit and a preestablished distal limit.

7. The mechanism of claim 6, wherein the cannula is configured to receive an endoscope.

8. The mechanism of claim 1, wherein the rigidizing actuator transitions the plurality of serially arranged links between rigidized and non-rigidized states.

9. The mechanism of claim 8, wherein the rigidizing actuator operates upon application of pressure or vacuum to transition the plurality of serially arranged links.

10. The mechanism of claim 1, wherein the plurality of serially arranged links are rigidized in response to applying tension to the cable.

11. The mechanism of claim 1, wherein the plurality of serially arranged links includes at least three links.

12. A system for modifying a rigidizing force on a steerable elongate body deliverable within a body cavity, the system comprising:
an elongate body comprising a plurality of serially arranged links comprising a distal link and a link proximal to the distal link; and
a cable extending along the plurality of serially arranged links, the cable having a proximal end and a distal end, wherein the proximal end is coupled to an actuator outside of the elongate body, wherein the cable interacts with the distal link of the plurality of serially arranged links, and wherein the distal end is coupled to the link proximal to the distal link of the plurality of serially arranged links;
wherein the plurality of serially arranged links is placed between rigidized and nonrigidized states based on tension in the cable; and
wherein a longitudinal axis of the plurality of serially arranged links is configurable into differing shapes in the nonrigidzed state and is held in a respective shape in the rigidized state.

13. The system of claim 12, wherein the distal link comprises a pulley, and wherein the cable interacts with the pulley.

14. The system of claim 12, wherein the distal link comprises a fixed ferrule or loop back, and wherein the cable interacts with the fixed ferrule or loop back.

15. The system of claim 12, wherein the elongate body is a cannula.

16. The system of claim 15, wherein the cannula is configured to receive a device and to interact with a limiting coupling affixed to the device to prevent the cannula from sliding over the device beyond a preestablished proximal limit and a preestablished distal limit.

17. The system of claim 16, wherein the cannula is configured to receive an endoscope.

18. The system of claim 12, wherein the actuator transitions the plurality of serially arranged links between the rigidized and non-rigidized states.

19. The system of claim 12, wherein the plurality of serially arranged links includes at least three links.

20. The system of claim 12, further comprising a steerable tip extending through the elongate body, wherein the steerable tip and the elongate body are configured to be extended and retracted relative to one another.

* * * * *